(12) United States Patent
Chu

(10) Patent No.: US 8,409,075 B2
(45) Date of Patent: Apr. 2, 2013

(54) TUBULAR IMPLANTABLE SLING AND RELATED DELIVERY SYSTEMS, METHODS AND DEVICES

(75) Inventor: Michael S. H. Chu, Brookline, MA (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 78 days.

(21) Appl. No.: 12/906,531

(22) Filed: Oct. 18, 2010

(65) Prior Publication Data
US 2011/0028779 A1 Feb. 3, 2011

Related U.S. Application Data

(62) Division of application No. 11/201,847, filed on Aug. 11, 2005, now Pat. No. 7,815,562.

(51) Int. Cl.
*A61F 2/02* (2006.01)

(52) U.S. Cl. .......................................................... 600/30
(58) Field of Classification Search ............. 600/29–32, 600/37; 128/885, 898
See application file for complete search history.

(56) References Cited

U.S. PATENT DOCUMENTS

| | | | |
|---|---|---|---|
| 6,387,041 B1 * | 5/2002 | Harari et al. ................... 600/30 |
| 7,364,541 B2 * | 4/2008 | Chu et al. ........................ 600/30 |
| 8,128,554 B2 * | 3/2012 | Browning ........................ 600/37 |
| 2002/0161382 A1 * | 10/2002 | Neisz et al. ................... 606/151 |

* cited by examiner

*Primary Examiner* — John Lacyk
(74) *Attorney, Agent, or Firm* — Bingham McCutchen LLP

(57) ABSTRACT

The invention generally relates to surgically implantable supportive slings. More specifically, in various embodiments, the invention is directed to systems, devices and methods relating to a surgically implantable supportive sling having an adjustable shape.

17 Claims, 6 Drawing Sheets

TUBULAR IMPLANTABLE SLING AND RELATED DELIVERY SYSTEMS, METHODS AND DEVICES

This application is a divisional of U.S. application Ser. No. 11/201,847, filed Aug. 11, 2005 now U.S. Pat. No. 7,815,562, is incorporated by reference in its entirety.

FIELD OF THE INVENTION

The invention generally relates to surgically implantable supportive slings. More specifically, in various embodiments, the invention is directed to systems, devices and methods relating to a surgically implantable shape adjustable supportive sling.

BACKGROUND

Urinary incontinence affects over 13 million men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI is the use of a sling, which is permanently placed under a patient's bladder neck or mid-urethra to provide a urethral platform. Placement of the sling limits the endopelvic fascia drop, while providing compression to the urethral sphincter to improve coaptation. Generally, the sling is surgically placed under urethra, close to the high-pressure zone with no elevation of the urethra. The ends of a sling are secured to an anatomical location by, for example, a bone anchor. Recent advances in surgical techniques have demonstrated the effectiveness of approaches without employing bone anchors toward mid-urethra sling stabilization. However, the bone anchor-less techniques typically require the use of large diameter delivery devices. For example, some procedures require ⅛ to ¼ inch diameter delivery devices to create a tract in which the sling would lie. Such a large tract may cause the patients pain for weeks. Further, the typical sling made from woven mesh may also narrow when tensioned during placement, which results in less stable placement in tissue.

Accordingly, there is a need for an improved surgically implantable sling or sling-like support having a low profile, and which does not narrow during placement.

SUMMARY OF THE INVENTION

The invention addresses the deficiencies of the prior art by providing improved devices, systems and methods relating to an implantable sling for supporting an anatomical site in the body of a patient. More particularly, in various embodiments, the invention provides a supportive sling that can be inserted into the body of a patient in a low width state, and subsequent to insertion into the body, can be reconfigured to have a larger width sized appropriately for supporting the anatomical site. According to one embodiment, in the low width state, the sling has an increased length. As the length is decreased subsequent to insertion, the width increases. According to one advantage, the sling can be transitioned from between the first and second states without damaging the sling. According to another advantage, the transitioning between the first and second states also provides a mechanism for tensioning the sling under the anatomical site being supported. The sling of the invention may be used to support any suitable internal anatomical site. However, in some embodiments, the sling of the invention may be employed, for example, for providing a urethral support to treat urinary incontinence or for pelvic floor reconstruction.

In one aspect, a sling assembly of the invention includes an implantable supportive sling having a tubular shape defining an outer side for supporting an anatomical site in a patient, an inner side and an axial passage extending on the inner side between first and second ends. The sling assembly also includes a first tensioning filament attached at the first end of the sling and extending through the axial passage and out the second end of the sling, and a second tensioning filament attached to the second end of the sling and extending through the axial passage and out the second end of the sling.

According to one embodiment, the sling assembly includes a first tensioning filament attached at the first end of the sling, extending through the axial passage, and out the sling mesh at a point other than the second end of the sling. For example, the first tensioning filament may extend through the axial passage and out the sling mesh at approximately the midpoint of the sling. The sling assembly further includes a second tensioning filament attached to the second end of the sling, extending through the axial passage, and out the sling mesh at a point other than the second end of the sling. For example, the second tensioning filament may extend through the axial passage and out the sling mesh at approximately the midpoint of the sling.

According to one embodiment, the sling assembly also includes a first end cap attached to the first end of the sling and a second end cap attached to the second end of the sling, the first and second end caps having through apertures. In one configuration, the first tensioning filament attaches to the first end of the sling by way of the first end cap and extends out of the second end of the sling by way of the through aperture of the second end cap. Similarly, the second tensioning filament attaches to the second end of the sling by way of the second end cap and extends out of the first end of the sling by way of the through aperture of the first end cap. According to a further configuration, the first and second filaments attach to inner surfaces of the respective first and second end caps. In some configurations, the end caps are tapered to provide tissue dilation during insertion of the sling assembly ends into the body of the patient.

In operation, pulling on a terminal end of the first tensioning filament while holding a terminal end of the second tensioning filament stationary draws the first end cap axially along the second tensioning filament to effectively shorten the length of the sling. Due to the tubular configuration of the sling, this pulling also causes the width of the sling along at least a middle portion to widen. Similarly, pulling on the terminal end of the second tensioning filament while holding the terminal end of the first tensioning filament stationary draws the second end cap axially along the first tensioning filament, once again to effectively shorten the length and increase the width of the sling.

The sling of the sling assembly may be made of any suitable material. However, in preferred embodiments, the sling is formed from a woven or mesh material. The woven or mesh material enables the sling to transition easily between various lengths and widths as described above, without twisting, folding or otherwise becoming tangled, damaged or undesirably distorted.

According to a further embodiment, the sling assembly may include any suitable association mechanisms attached to the terminal ends of the first and second tensioning filaments for associating the sling assembly of the invention with a suitable delivery device. At one end of the spectrum, such association mechanisms may provide, for example, relatively loose slidable associations with a delivery device, or alternatively, relatively secure, fixed attachments to such delivery devices. According to one embodiment, first and second soft tissue anchors attach to respective terminal ends of the first and second tensioning filaments. Any suitable delivery device may engage with the soft tissue anchors to deliver them to a desired anatomical location.

According to a further aspect, the invention provides a delivery device for delivering the sling assembly of the invention to a desired anatomical location. In this aspect, the delivery device includes a handle, and a shaft extending distally from a distal end of the handle. The shaft includes a shaft lumen axially extending near a distal end of the shaft, the shaft lumen being sized and shaped for slidably receiving an anchor of a sling assembly. The shaft also includes a slot extending axially along at least a portion of the shaft lumen, the slot being sized and shaped for slidably receiving a filament attached to the anchor received in the shaft lumen.

According to one embodiment, the shaft lumen extends axially into the shaft from an opening in the distal end of the shaft, with the opening being sized and shaped for receiving the anchor of the sling assembly into the shaft lumen. In one configuration, the slot extends axially in a proximal direction from the opening in the distal end of the shaft. According to one construction, the slot extends proximally for an entire length of the shaft lumen. However, in an alternative construction, the slot extends proximally for only a portion of the length of the shaft lumen.

According to another embodiment, the handle includes a handle lumen extending axially through the handle and the shaft lumen extends distally to a distal end of the shaft and axially aligns with the handle lumen. According to one feature of this embodiment, the delivery device includes a pusher assembly. The pusher assembly includes a pusher and a user actuator for sliding the pusher axially within the shaft and handle lumens.

According to a further embodiment, the delivery device includes a notch having a width greater than the width of the slot, located along a portion of the shaft lumen, and extending axially from an end of the slot. The notch may extend proximally from a proximal end of the slot or distally from a distal end of the slot. According to various configurations, the shaft lumen may extend distally from a distal end of the notch or proximally from a proximal end of the notch. In some embodiments, the shaft lumen extends distally to an opening in a distal end of the shaft. Preferably, the opening is sized and shaped for receiving the anchor of the sling assembly into the shaft lumen. According to one feature, the delivery device of this embodiment includes an alternative pusher sized and shaped for insertion into the opening in the distal end of the shaft and for extending at least to a distal end of the notch.

According to another aspect, the shaft of the delivery device of the invention includes a shaft lumen axially extending near a distal end of the shaft, with the shaft lumen sized and shaped for slidably interfitting with an anchor of a sling assembly. The shaft also includes a notch extending axially along at least a portion of the shaft lumen, with the notch sized and shaped for receiving an anchor of a sling assembly into the shaft lumen. In one embodiment of this aspect, the handle of the delivery device includes a handle lumen extending axially through the handle, and the shaft lumen extends distally to a distal end of the shaft and axially aligns with the handle lumen. According to a further embodiment, the delivery device includes a cannula assembly, the cannula assembly including a cannula and a user actuator for sliding the cannula axially within the shaft and handle lumens at least partially into the notch.

According to another aspect, the invention provides a system for treating urinary incontinence. The system includes a sling assembly, which includes an implantable supportive sling having a tubular shape defining an outer side for supporting a urethra of a patient, an inner side and an axial passage extending on the inner side between first and second ends, a first tensioning filament attached at the first end of the sling and extending through the axial passage and out the second end of the sling, and a second tensioning filament attached to the second end of the sling and extending through the axial passage and out the second end of the sling. The system further includes a delivery device for implanting the sling in periurethral tissues of the patient to ameliorate urinary incontinence.

According to one embodiment, a sling assembly of a system of the invention includes a first anchor attached to a terminal end of the first tensioning filament and a second anchor attached to a terminal end of the second tensioning filament.

According to one embodiment, a delivery device of a system of the invention includes a handle and a shaft extending distally from a distal end of the handle and including, a shaft lumen axially extending near a distal end of the shaft, the shaft lumen being sized and shaped for slidably receiving at least one of the first and second anchors of the sling assembly, and a slot extending axially along at least a portion of the shaft lumen, the slot being sized and shaped for slidably receiving at least one of the first and second tensioning filaments.

According to another embodiment, a delivery device of a system of the invention includes a handle and a shaft extending distally from a distal end of the handle and including, a shaft lumen axially extending near a distal end of the shaft, the shaft lumen being sized and shaped for slidably interfitting with at least one of the first and second anchors of the sling assembly, and a notch extending axially along at least a portion of the shaft lumen, the notch being sized and shaped for receiving at least one of the first and second anchors of a sling assembly into the shaft lumen.

A further aspect of the invention provides a method for treating urinary incontinence or for pelvic floor reconstruction. According to one embodiment, a method of the invention includes delivering a first end of a sling assembly including a first end of a supportive sling to a first anatomical site in a body of a patient. The method includes delivering a second end of the sling assembly to a second anatomical site in the patient to draw the first end of the supportive sling along a tensioning filament attached to the second end of the sling assembly to reduce a length and increase a width of the sling as distance increases between the first and second anatomical sites to ameliorate urinary incontinence.

The foregoing and other objects, features, and advantages of the invention will become more apparent from the following description and from the claims.

BRIEF DESCRIPTION OF THE DRAWINGS

Various illustrative systems, methods, devices, features and advantages of the invention are described below with reference to the appended drawings, which may not be drawn to scale and in which like parts are designated by like reference designations.

FIG. 1A depicts a tubular sling assembly in an unexpanded state according to an illustrative embodiment of the invention.

DESCRIPTION OF ILLUSTRATIVE EMBODIMENTS

As described in summary above, in various illustrative embodiments, the invention is directed to a sling assembly including a supportive and implantable sling having tubular configuration in which filaments may be operator actuated to transition the sling from an elongated width-contracted state to a shorter width-expanded state. In other illustrative embodiments, the invention is directed to delivery devices for delivering the sling of the invention, anchors for anchoring the sling in place, various association members for associating the sling assembly of the invention with a suitable delivery device, and kits including a delivery device and sling assembly of the invention.

Figure 1A:
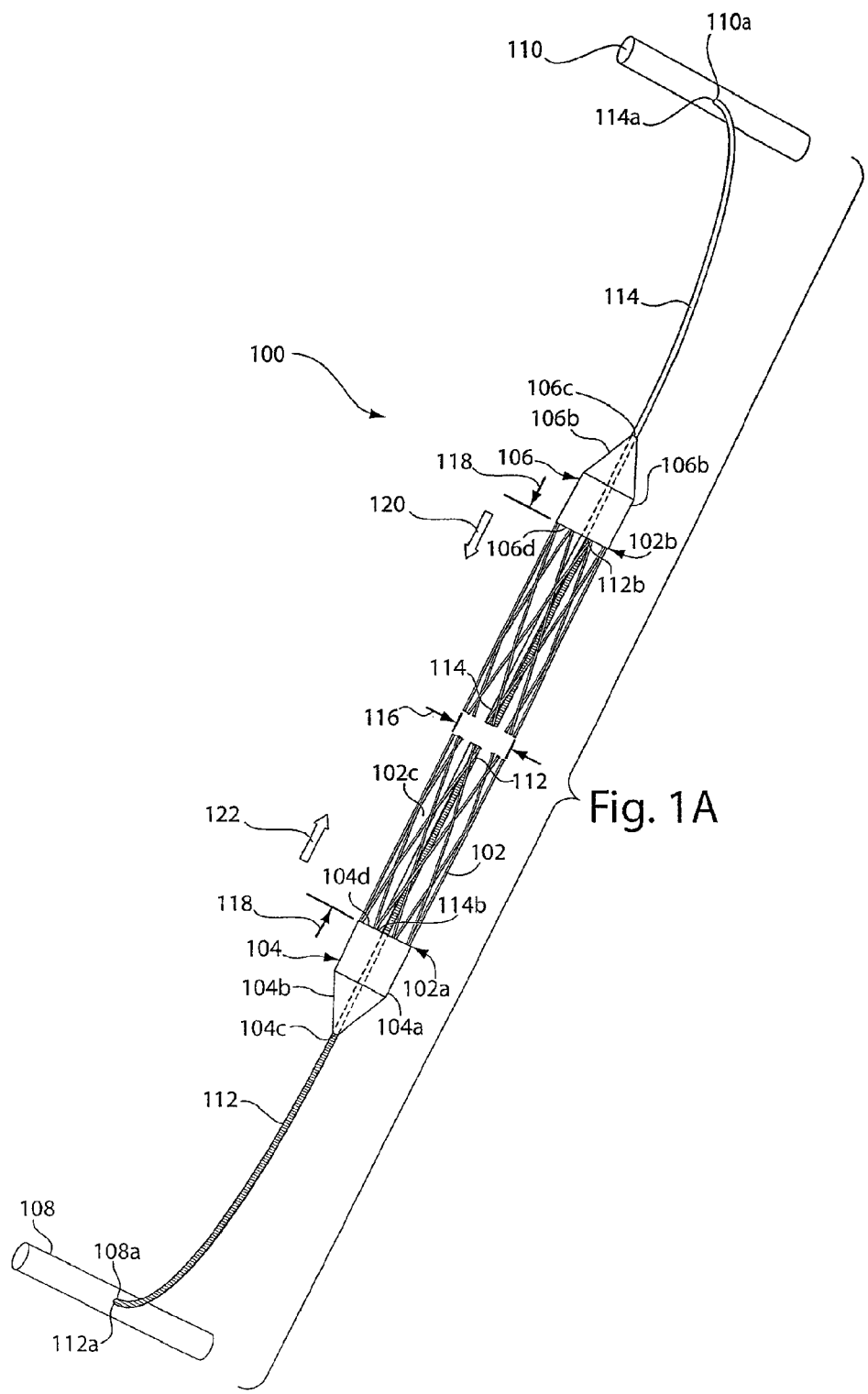
FIG. 1B depicts a tubular sling assembly in an expanded state according to an illustrative embodiment of the invention.
FIG. 1C depicts a tubular sling assembly in an expanded state according to an alternative illustrative embodiment of the invention.
Figure 1B:
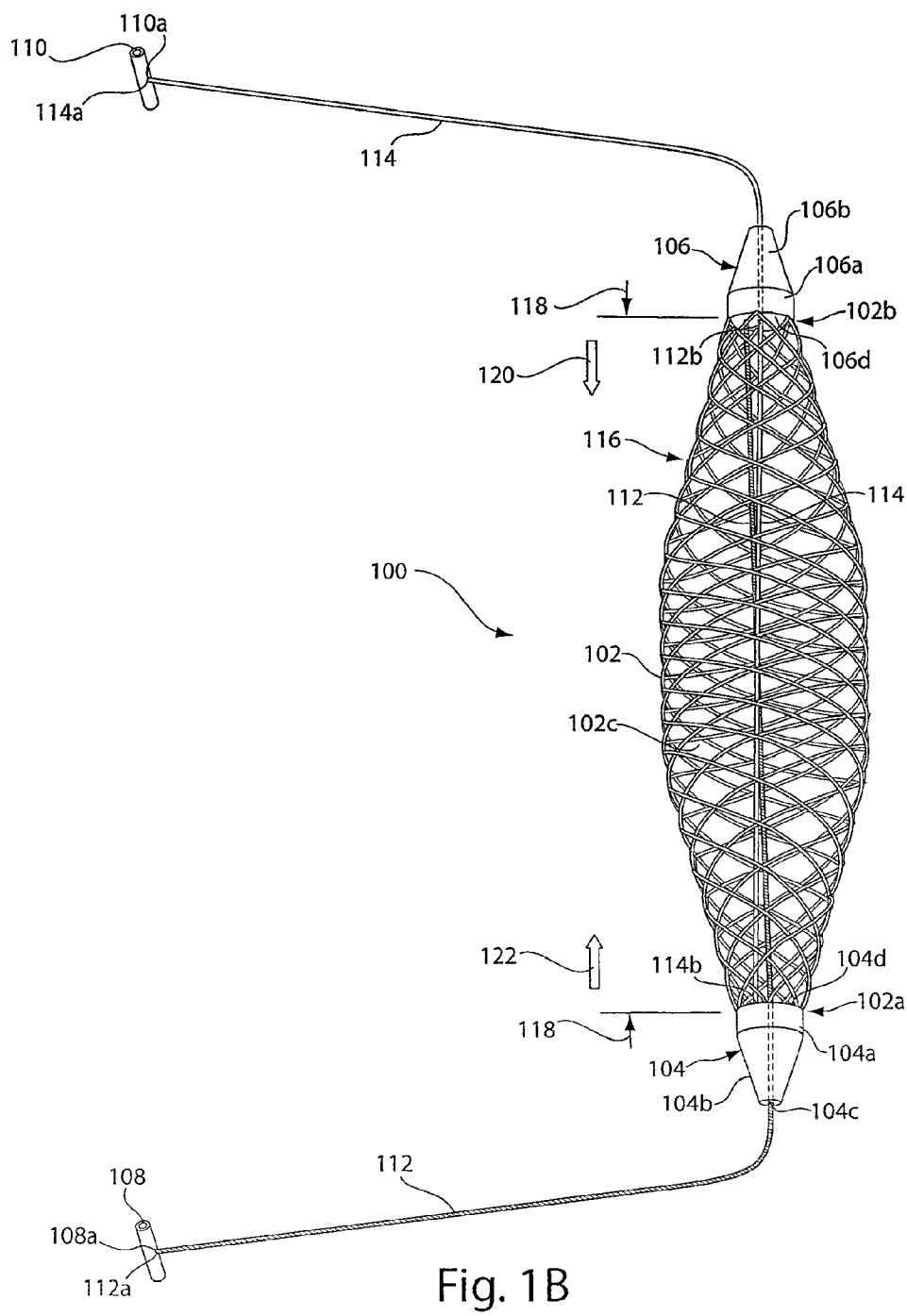
Figure 1C:
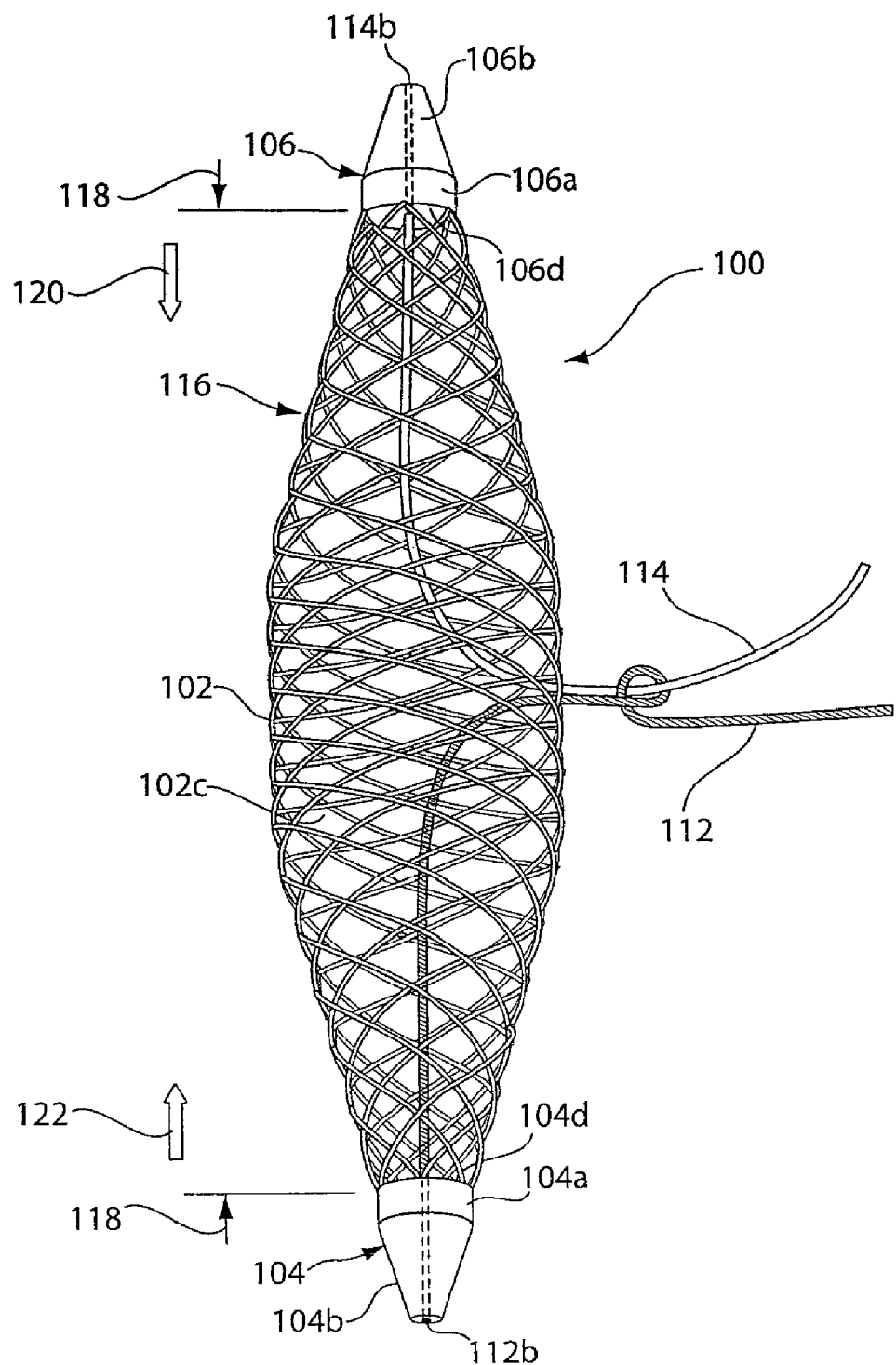

FIG. 1A depicts a sling assembly 100 in an untensioned state according to an illustrative embodiment of the invention. As shown, the sling assembly 100 includes: a tubular and implantable sling 102; two dilators 104 and 106 located at either end 102a and 102b, respectively, of the sling 102; two anchors 108 and 110; and two tensioning filaments 112 and 114. FIG. 1B depicts the sling 100 in a more or fully tensioned state according to an illustrative embodiment of the invention. FIG. 1C depicts the sling assembly 100 in a more or fully tensioned state according to an alternative illustrative embodiment of the invention.

Referring to FIGS. 1A, 1B, and 1C, the dilator 104 has a generally cylindrical portion 104a and a generally conical portion 104b extending axially from the cylindrical portion 104a. The conical portion 104b tapers smaller toward and terminates in an aperture 104c. A terminal end 104d of the cylindrical portion 104a bonds to the end 102a of the tubular sling 102. Bonding may be accomplished by way of any suitable approach, including gluing, heat bonding and/or tying. In the illustrative example, the dilator 104 is hollow. Similarly, the dilator 106 has a generally cylindrical portion 106a and a generally conical portion 106b extending axially from the cylindrical portion 106a. The conical portion 106b tapers smaller toward and terminates in an aperture 106c. A terminal end 106d of the cylindrical portion 106a bonds to the end 102b of the tubular sling 102. As in the case of the sling end 102a, bonding may be accomplished by way of any suitable approach, including gluing, heat bonding and/or tying. In the illustrative example, the dilator 106 is also hollow. It should be noted that although the illustrative embodiment depicts the sling assembly as including the dilators 104 and 106, this need not be the case. By way of example, any suitable end caps 104 and 106 may be used, which may or may not provide a tissue dilation function. Additionally, no end caps 104 and 106 at all may be employed, instead attaching the dilator ends of the below described filaments to the sling ends themselves.

The sling 102 is depicted as being formed from a synthetic mesh, but this need not be the case. The sling 102 may be formed from any suitable material, synthetic, natural (e.g., biological) or a combination thereof. The sling also need not be configured as a mesh. An important feature of the sling 102 is that it has multiple shape states. Thus, any material that provides the same or similar shape states may be employed. More specifically, the sling 102 may be in an untensioned state, fully tensioned or any state in between. The sling may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials can include polyglycolic acid, polylactic acid, and other suitable absorbable synthetic materials. Alternatively, the material for the sling may be derived from mammalian tissue(s) or a combination of mammalian tissue(s) and synthetic material(s). The sling material may be fabricated from one or more yarns, which yarns may be made from one or more materials. The sling may incorporate or be coated with one or more agents to provide a therapeutic effect, for example, to reduce discomfort, to reduce the chance of infection and/or to promote tissue growth.

In the untensioned state of FIG. 1A, the sling 102 has a diameter 116 near a mid point, which is smaller than a similarly central diameter, such as the diameter 116 of FIG. 1B, taken in a more or fully tensioned state. Also, in the untensioned state of FIG. 1A, the sling 102 has a length 118, which is longer than a length, such as the length 118 of FIG. 1B, taken in the more or fully tensioned state. Thus, as the sling becomes more tensioned, its diameter (which translates into its width when the sling is fattened) expands and its length contracts. Similarly, as the sling becomes less tensioned, its length expands and its diameter contracts. According to the illustrative embodiment, the length 118 of the sling 102 in the narrowed state of FIG. 1A is between about 9 cm to about 13 cm, and is between about 5 cm to about 9 cm in the widened state of FIG. 1B. In one illustrative embodiment, the length 117 of FIG. 1A is about 7 cm. According to a further illustrative embodiment, the length 118 of FIG. 1B is about 11 cm.

Another important feature of the sling 102 is that its tubular configuration provides an axially extending passage 102c through which the filaments 112 and 114 pass. As shown, the filament 112 has an anchor end 112a and a sling end 112b. The sling end 112b of the filament 112 threads into the dilator 104 through the aperture 104c in the conical portion 104b, through the hollow body of the dilator 104 and out the cylindrical end 104d of the dilator 104. The aperture 104c and the filament 112, illustratively, are sized to enable the filament 112 to slide easily through the aperture 104c. The sling end 112b of the filament 112 then threads axially through the passage 102c in the cylindrically configured sling 102, through the cylindrical end 106d of the dilator 106, and anchors to the dilator 106. In the illustrative embodiment, the sling end 112b of the filament 112 is glue bonded to an inner surface of the cylindrical end 106d of the dilator 106. However, the filament end 112b may be bonded to the dilator 106 in any suitable manner and to any suitable location on the dilator 106. By way of example, the filament end 112b may be tied, heat bonded or formed integrally with the dilator 106.

The anchor end 112a of the filament 112 attaches to the anchor 108. The anchor 108 may be of any suitable shape. In the illustrative embodiment of FIGS. 1A and 1B, the anchor 108 is cylindrical and hollow in nature, about 2 cm long and has a through aperture 108a in a side wall. The filament end 112a interfits through the aperture 108a and is bonded within the anchor 108. The filament end 112a may be bonded with the anchor 108 in any suitable manner, including without limitation, glue bonded, tied, knotted or crimped. The filament 112 is preferably formed from a flexible polymer or metal. In some illustrative embodiments, it may be formed from any suitable suturing material. With the aperture 108a located near a middle location along a length of the anchor 108, the anchor 108 tends to form a T-configuration with the filament 112, which tends to resist removal of the sling 102 when embedded in soft tissue.

In a similar fashion to the filament 112, and as shown in FIGS. 1A and 1B, the filament 114 has an anchor end 114a and a sling end 114b. The sling end 114b of the filament 114 threads into the dilator 106 through the aperture 106c in the conical portion 106b, through the hollow body of the dilator 106 and out the cylindrical end 106d of the dilator 106. The aperture 106c and the filament 114, illustratively, are sized to enable the filament 114 to slide easily through the aperture 106c. The sling end 114b of the filament 114 then threads axially through the passage 102c in the cylindrically configured sling 102, through the cylindrical end 104d of the dilator 104, and anchors to the dilator 104. In the illustrative embodiment, the sling end 114b of the filament 114 is glue bonded to an inner surface of the cylindrical end 104d of the dilator 104. However, the filament end 114b may be bonded to the dilator 104 in any suitable manner and to any suitable location on the dilator 104. By way of example, the filament end 114b may be tied, heat bonded or formed integrally with the dilator 104.

The anchor end 114a of the filament 114 attaches to the anchor 110. As in the case of the anchor 108, the anchor 110 may be of any suitable shape. In the illustrative embodiment of FIGS. 1A and 1B, the anchor 110 is cylindrical and hollow in nature, about 2 cm long and has a through aperture 110a in a side wall. The filament end 114a interfits through the aperture 110a and is bonded within the anchor 110. The filament end 114a may be bonded with the anchor 110 in any suitable manner, including without limitation, glue bonded, tied, knotted or crimped. The filament 114 is preferably formed from a flexible polymer or metal. In some illustrative embodiments, it may be formed from any suitable suturing material.

In operation, pulling on the filament 112, while holding the anchor 110 (and thus, the filament 114) stationary, pulls the dilator 106 along the filament 114 in the direction indicated by the arrow 120, causing the length 118 of the sling 102 to decrease, for example, from that shown in FIG. 1A to that shown in FIG. 1B. It also causes the diameter 116 to increase, for example, from that shown in FIG. 1A to that shown in FIG. 1B.

In a similar fashion, pulling on the filament 114, while holding the anchor 108 (and thus, the filament 112) stationary, pulls the dilator 104 along the filament 112 in the direction indicated by the arrow 122, also causing the length 118 of the sling 102 to decrease, for example, from that shown in FIG. 1A to that shown in FIG. 1B. It also causes the diameter 116 to increase, for example, from that shown in FIG. 1A to that shown in FIG. 1B. Pulling on both filaments 112 and 114 also has similar effects on the sling length 118 and sling width 116. This feature enables the sling 102 to be sized, shaped and tensioned in a custom manner, both prior and subsequent to delivery to an anatomical site, such as the periurethral tissue in the body of a patient.

FIG. 1C depicts a sling assembly 100 according to an alternative illustrative embodiment of the invention. In contrast to FIG. 1B, the end 112b of the filament 112 attaches to the dilator 104, and the end 114b of the filament 114 attaches to the dilator 106. In this alternative configuration, the filament ends 112a and 114a thread through the sling 102 and out the sling mesh at an intermediate location between the dilators 104 and 106. According to the illustrative embodiment of FIG. 1C, the filament ends 112a and 114a emerge from the sling mesh 102 at approximately a midpoint between the dilator 104 and the dilator 106. However, this need not be the case.

According to the illustrative embodiment of FIG. 1C, the filaments 112 and/or 114 can be adjusted, for example, via a vaginal incision subsequent to implementation, to position and/or tension the sling 102. The filament ends 112a and 114a also can be tied, knotted, crimped, or otherwise bonded to maintain the correct tension and position of the sling 102. This also maintains the length 118 and the width 116 of the sling 102.

A tubular sling assembly of the invention may also include a sleeve for covering, at least partially, the tubular sling 102 during implantation. The sleeve may be made, for example, from one or more absorbent materials, such as a sponge-like material, that can optionally be pre-soaked in a drug solution, for example, in an anesthetic, anti-inflammatory, coagulating, anticoagulating, or antibiotic solution. In another embodiment, the sleeve may be made from a non-wettable material, such as polypropylene, polyethylene, polyester, polytetrafluoroethylene (available from DuPont Corporation, Wilmington, Del., under the trademark TEFLON®), TYVEK®, MYLAR®, or co-polymers thereof. The non-wettable materials can also be pretreated with a therapeutically effective drug coating. The sleeve is preferably transparent so that an operator will be able to see the implantable, tubular sling inside the sleeve. The sleeve is also preferably made from expandable materials such that it will not constrain the expansion of the tubular sling enclosed, at least partially, therein.

According to the illustrative embodiment, the diameter 116 of the tubular sling 102 is about 0.5 cm to about 2 cm before expansion, and the length 118 is about 4 cm to about 20 cm length before expansion. In other embodiments, the diameter 116 is less about 0.5 cm, 0.4 cm, 0.3 cm, or 0.2 cm. The dilators 106 and 108 may have similar outside diameters to that of the sling 102. In certain embodiments employing a sleeve covering, at least partially, the sling, the sling ends do not attached to the sleeve. This feature enables a medical operator to pull on the ends of the sleeve during sling assembly placement, and/or any of the delivery devices if associated with the sleeve rather than the sling, without risk of stretching, curling or otherwise deforming the sling 102. In certain so illustrative embodiments, the sleeve employed with the tubular sling 102 is bioabsorpable or biodegradable.

According to various illustrative embodiments, the sling 102, after expansion, has a length 118 of about 5 cm to about 15 cm and a width 116 of about 1 cm to about 5 cm, though the length and width of the sling may have any suitable dimensions depending on the body part to be supported.

Figure 2:
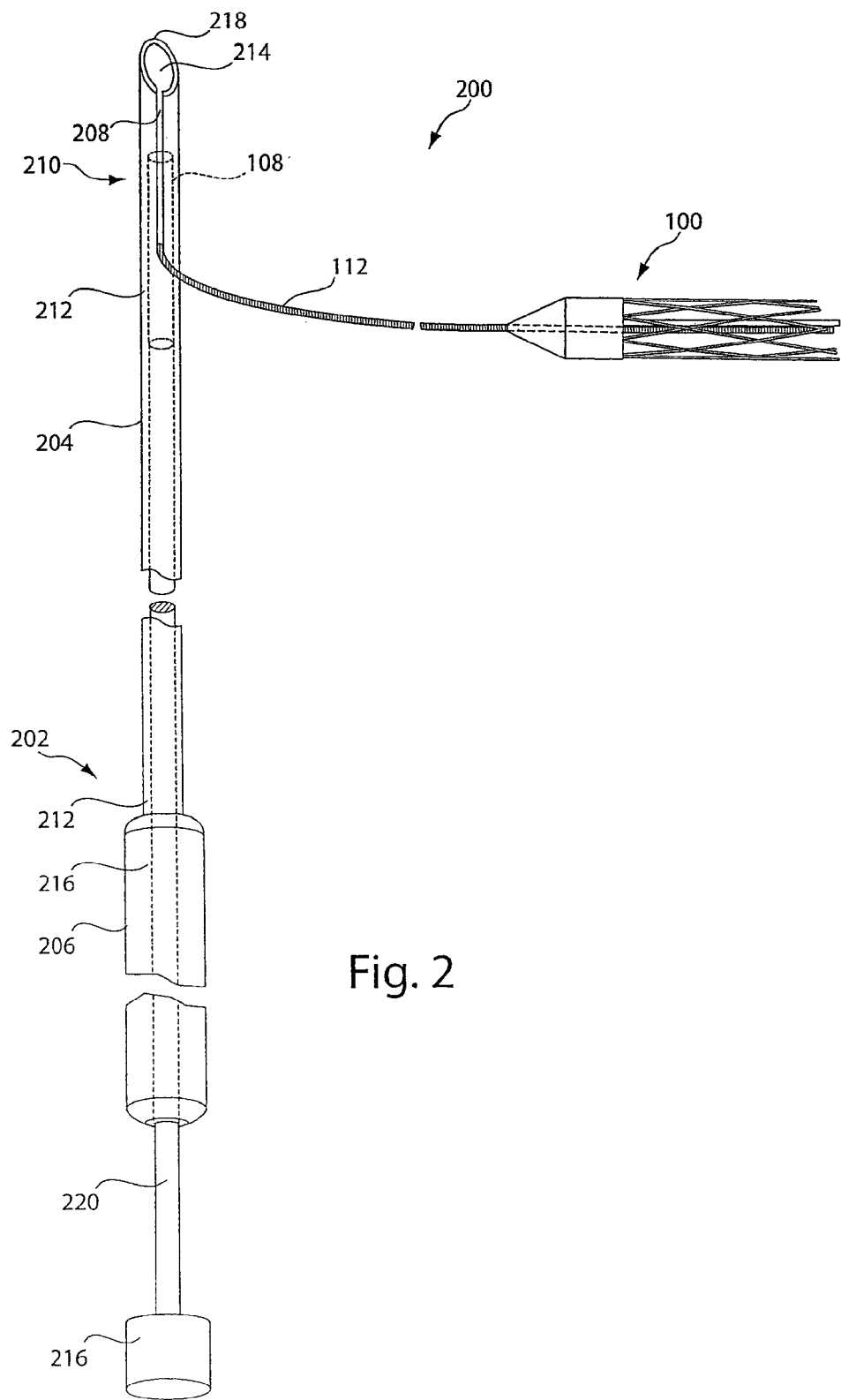
FIG. 2 depicts a system for delivering a tubular sling assembly to an anatomical site including a delivery device having a shaft with an axially extending slot in a distal portion for engaging with a T-anchor and tensioning suture of the sling assembly according to an illustrative embodiment of the invention.

FIG. 2 depicts a system 200 for delivering the tubular sling assembly 100 of FIGS. 1A and 1B to an anatomical site including a delivery device 202 having a shaft 204 with an axially extending slot 208 in a distal portion 210 of the shaft 204 for engaging with the T-anchor 108 and tensioning filament 112 of the sling assembly 100 according to an illustrative embodiment of the invention. As depicted, the delivery device 202 includes a use actuator 216 at the proximal end, an actuatable pusher 220, a handle 206, and the shaft 204 extending distally from a distal end of the handle 206. A shaft lumen 212 extends axially into the shaft 204 from an opening 214 at a distal end of the shaft 204 and through the shaft 204. The shaft lumen 212 is sized and shaped for slidably receiving the T-anchor 108 of the sling assembly 100, as depicted. The slot 208 extends axially into the shaft 204 from the opening 214 along a distal portion of the shaft lumen 212. The slot 208 is sized and shaped for slidably receiving the tensioning filament 112 of the sling assembly 100. A handle lumen 216 extending axially through the handle 206 and axially aligns with the shaft lumen 212. The pusher 220, by way of the user actuator 216, slides axially within the handle lumen 216 and the shaft lumen 212. The pusher 220 is sized and shaped such that, when actuated by way of the user actuator 216, it can engage with the T-anchor 108, slide the T-anchor 108 distally and out of the shaft lumen 212 through the opening 214.

In use, an operator may slide the T-anchor 108 into the shaft lumen 212 from the opening 214 of the shaft 204 and further slide the T-anchor 108 distally such that the tensioning filament 112 is received by the slot 208. To dissociate the T-anchor 108 and thus the sling assembly 100 from the delivery device 202, the operator can actuate the user actuator 216 and slide the pusher 220 distally along the handle lumen 216 and the shaft lumen 212 to push the T-anchor 108 out of the shaft lumen 212 through the opening 214. An advantage of the slot 208 and the shaft 204 design is that the T-anchor 108 can remain free to slide along the slot 208. When slid to a proximal most position in the slot 208 during the insertion of the delivery device 202 into a body of a patient, the T-anchor 108 remains engaged with the slot 208 such that the sling assembly 100 remains associated with the delivery device 202. During withdrawal of the delivery device 202, the T-anchor 108 can be, by way of the user actuator 216 and the pusher 220, easily slid distally off the shaft 204 of the delivery device 202, thus dissociating the sling assembly 100 from the delivery device 202 and leaving the T-anchor 108 in an anatomical site of the patient.

The depicted configuration is suitable for delivering a sling assembly with a transvaginal, prepubic, or inside-out transobtural approach, which includes associating the sling assembly 100 with the delivery device 202 before inserting the delivery device 202 into a patient's body. For example, in a single-incision, prepubic approach, the deliver device 202, with the associated sling assembly 100, is inserted into a patient's body through a vaginal incision, and the T-anchor 108 is then placed at a desired anatomical location by actuating the pusher 220 to dissociate the T-anchor 108, thus the sling assembly 100, from the delivery device 202. The T-anchors may be delivered to any suitable location. By way of example, a medical operator may place the T-anchors, without limitation, between the ischiocavernous pubic muscle and ischiopubic bone; behind the pubic bone; in front of, embedded within, or through the obturator membrane; or within any suitable ligaments or other tissue structures.

The delivery device 202 is then withdrawn from the patient's body. The same delivery device 202 or a different delivery device may be used to implant the other T-anchor 110, thus the entire sling assembly 100. The T-anchor 110 can be placed in a similar manner at an anatomical location on the opposite side of the urethra from the anatomical site where the T-anchor 108 is placed. During placement of the T-anchor 110, the tensioning filament 114 is being pulled, while the T-anchor 108, by way of tissue anchoring, effectively holds the tensioning filament 112 substantially stationary. Thus, implanting the T-anchor 110 to a desired anatomical site effectuates movement of the dilator 104 axially along the tensioning filament 112 to effectively shorten the length of the sling, resulting in widening of the sling 102 along at least a middle portion. The T-anchor 110, and thus the sling assembly 100, can then be dissociated from the delivery device, leaving the sling 102 implanted with a desirable length and width.

A sling assembly end may have other configurations, for example, the sling assembly end having a guide tube or an association tube as described in U.S. patent application Ser. No. 10/973,010. Similarly, a distal end or portion of a delivery device may have other configurations, for example, the delivery device having a shoulder near its distal end or a forked distal tip as described in U.S. patent application Ser. No. 10/973,010 or the delivery device having a L-slot located near its distal end, as described in U.S. patent application Ser. No. 10/957,926. The delivery device may also include a pusher assembly that interfits with and over the shaft of the delivery device, as described in U.S. patent application Ser. No. 10/973,010. All of the above applications are incorporated herein by reference.

Referring back to FIG. 2, the shaft 204 also includes a distal tip 218. As depicted, the distal tip 218 is sharp. However, a shaft of a delivery device of the invention may alternatively employ a different configuration. The distal tip or distal end of a shaft may be shaped to facilitate insertion of the shaft into the tissue of a patient, for example, being rounded, beveled, pointed, or any other suitable shape.

Also referring to FIG. 2, the shaft 204 and/or the handle 206 of the delivery device 202 are both substantially straight. However, in alternative embodiments, the shaft 204 and/or the handle 206 may include one or more curved sections. Additionally, the shaft 204 and/or the handle 206 may lie substantially in one plane or may be shaped to lie in multiple planes. The shaft 204 may be of substantially constant outside diameter or may include portions of differing outside diameters. In various embodiments, the shaft may include hooked and/or helical portions. The shaft may also be configured in various ways and/or include various features as described in the patents and patent applications referenced herein. Similarly, the handle 206 may also be configured in various ways and/or include various features as described in, e.g., U.S. Provisional Patent Application Ser. Nos. 60/508,600 and 60/569,300, the disclosures of which are incorporated herein by reference.

Figure 3:
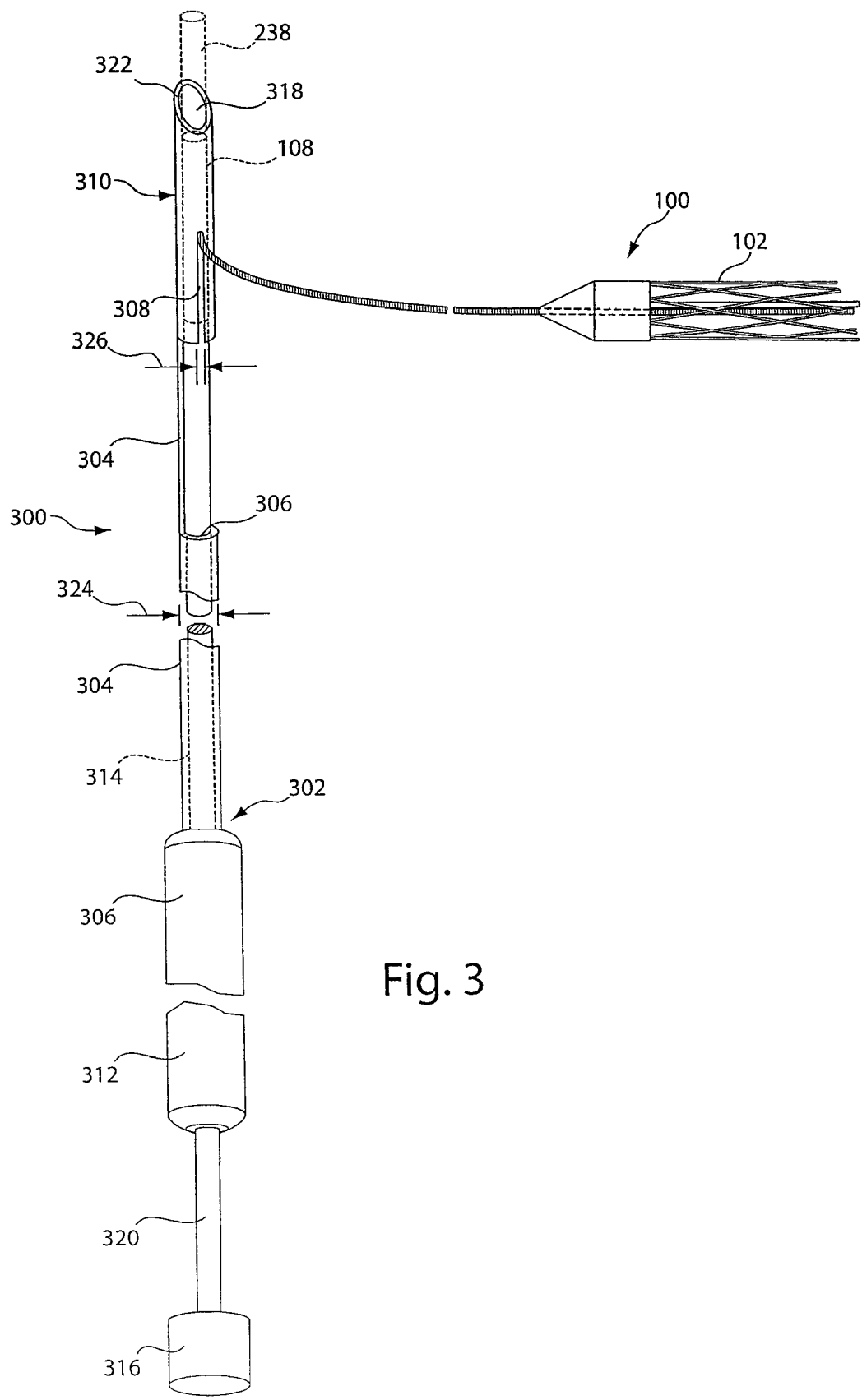
FIG. 3 depicts an alternative system for delivering a tubular sling assembly to an anatomical site including a delivery device having a shaft with a notch and at least one axially extending slot along a side of a distal portion for engaging with a T-anchor and suture of the sling assembly according to an illustrative embodiment of the invention.

FIG. 3 depicts an alternative system 300 for delivering the tubular sling assembly 100 to an anatomical site including a delivery device 302 having a shaft 304 with a notch 306 and at least one axially extending slot 308 along a side of a distal portion 310 for engaging with the T-anchor 108 and the tensioning filament 112 of the sling assembly 100 according to an illustrative embodiment of the invention. As depicted, the delivery device 302 includes, at its proximal end, a user actuator 316 and an actuatable pusher 320. The delivery device 302 further includes a handle 306 which has a handle lumen 312 extending axially through the handle 306. The shaft 304 extends distally from a distal end of the handle 306 and has a shaft lumen 314 extending axially through the shaft 304. The handle lumen 312 and the shaft lumen 314 axially align with each other such that the pusher 320 can be actuated, by way of the actuator 316, and slid axially within the handle lumen 312 and the shaft lumen 314.

Referring to FIG. 3, the slot 308 extends proximally for a distal portion of the shaft lumen 314. The slot 308 is sized and shaped for slidably receiving the tensioning filament 112 of the sling assembly 100. Unlike the slot 208 as depicted in FIG. 2, the slot 308 does not extend axially from a distal opening 318 of the shaft 304. The notch 306 extends axially from a proximal end of the slot 308 and has a width 324 that is larger than a width 326 of the slot 308. The notch 306 is located along a portion of the shaft lumen 314 and exposes that portion of the shaft lumen 314. The notch 306 is also sized and shaped for seating the T-anchor 108 within the exposed lumen of the shaft 314 and for easily removing the T-anchor 108 when the entire T-anchor 108 is located between a proximal end and a distal end of the notch 306.

In use, an operator may place the T-anchor 108 within the portion of the shaft lumen 314 exposed by the notch 306. By way of the actuator 316, the pusher 320 is slid distally and axially within the handle lumen 312 and the shaft lumen 314 and engages with the T-anchor 108 seated in the notch 306. By further sliding the pusher 320 distally, the T-anchor 108 is slid axially within the shaft lumen 314, and the tensioning filament 112 becomes engaged with the slot 308. To dissociate the T-anchor 108 from the delivery device 302, the operator can slide the pusher 320 proximally within the handle lumen 312 and the shaft lumen 314, by way of the actuator 316, thus causing the T-anchor 108 to slide distally within the shaft lumen 314 and move into the notch 306. The T-anchor 108 can easily disengage from the notch 306 when the entire length of the T-anchor 108 falls within a proximal end and a distal end of the notch 306.

As in the case of the delivery device 202 of FIG. 2, the depicted configuration of FIG. 3 is also suitable for delivering a sling assembly to an anatomical site in a patient's body by various approaches, for example, a transvaginal, inside-out transobturator, or prepubic approach. These approaches include associating a sling assembly end with a delivery device 302 before inserting the delivery device 302 into the patient's body through a vaginal incision. Alternatively, the delivery device 302 may be used to deliver a sling assembly to an anatomical site in a patient's body by a suprapubic (abdominal), outside-in transobtural, or top-down prepubic approach. Each of these approaches include inserting the delivery device 302 into the patient's body through an abdominal, ischiopubic, or other non-vaginal incision before associating a sling assembly end with the delivery device.

According to an alternative configuration, an external pusher 328 may be employed with the delivery device 302. In this configuration, the delivery device 302 may or may not include, at its proximal end, an actuator and an actuatable pusher, such as the depicted actuator 316 and the pusher 320. In use, an operator may place the T-anchor 108 in the notch 306 and slide the T-anchor 108 axially within the shaft lumen 314 to engage the tensioning filament 112 with the slot 308. To dissociate the T-anchor 108, and thus the sling assembly 100, from the delivery device 302, the operator slides the external pusher 328 into the shaft lumen 314 by way of the distal opening 318 of the shaft 304. The pusher 328 engages with the T-anchor 108, and further sliding of the pusher 328 proximally within the shaft lumen 314 causes the T-anchor 108 to slide proximally within the shaft lumen 314 and into the notch 306. The T-anchor 108 can easily disengage from the notch 306 when the entire length of the T-anchor 108 falls within a proximal end and a distal end of the notch 306.

As depicted, the notch 306 extends from a proximal end of the slot 308. According to an alternative configuration, a notch that is sized and shaped substantially the same as the notch 306 may extend from a distal end of a slot that extends along a side of a shaft of a delivery device and is sized and shaped substantially the same as the slot 308.

Figures 4, 5:
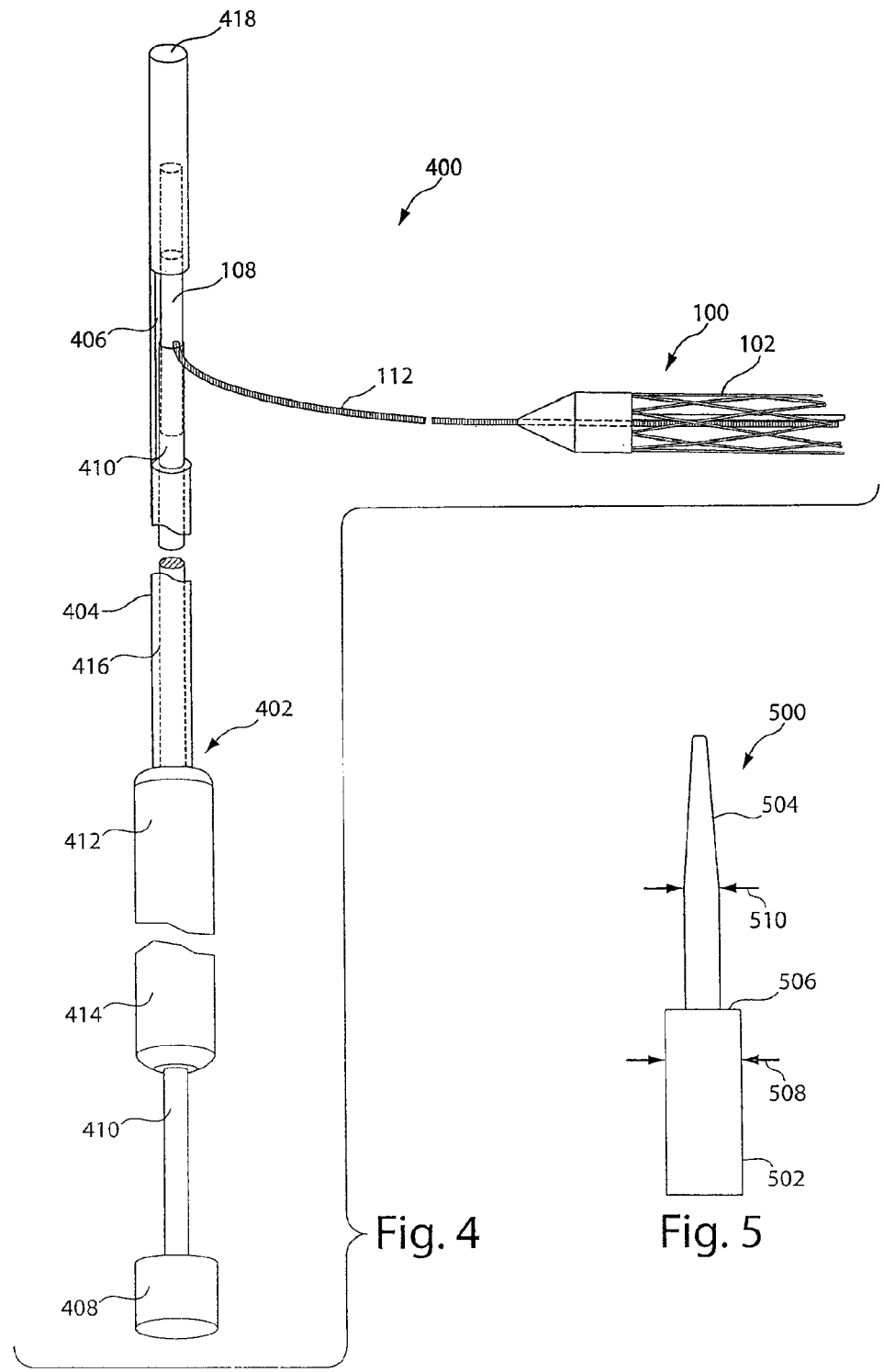
FIG. 4 depicts another alternative system for delivering a tubular sling assembly to an anatomical site including a delivery device having a hollow shaft with a notch along a side portion for seating a T-anchor and an inner cannula for extending within the hollow shaft and over the seated T-anchor to maintain the T-anchor within the shaft according to an illustrative embodiment of the invention.
FIG. 5 shows the distal end of an exemplary delivery device shaft for delivering a sling assembly of the type shown in FIG. 1C.

FIG. 4 depicts another alternative system 400 for delivering a sling assembly, such as the tubular sling assembly 100, to an anatomical site in a patient's body. The system 100 includes a delivery device 402 having a handle 412 and a shaft 404 extending distally from the handle 412. The handle 412 includes an axially extending through lumen 414. The shaft 404 also includes a lumen 416 in axially alignment with and extending distally from the handle lumen 414 along at least a portion of the length of the shaft 404. The shaft 404 includes a notch 406 that exposes a portion of the shaft lumen 416, and is sized and shaped to readily receive and release the T-anchor 108. The delivery device 402 includes a cannula assembly, which has a user actuator 408 located at a proximal end of the delivery device 402, and a cannula 410 extending distally from the actuator 408 through the handle lumen 414 and the shaft lumen 416. The cannula 410 is sized and shaped such that, in response to the actuator 408 being pushed in a distal direction, the cannula 410 extends into the notch 406 to interfit over and cover at least proximal portion of the T-anchor 108 to capture the T-anchor 108 within the notch 406.

In use, when the notch 406 is not covered by the cannula 410, an operator can associate the sling assembly 100 with the delivery device 402 by placing the T-anchor 108 within the notch 406. The operator may then actuate the cannula 410 and slide it distally within the handle lumen 414 and the shaft lumen 416 and into the notch 406 to interfit over and cover at least the proximal portion of the T-anchor 108. The sling assembly 100 remains associated with the delivery device 402 in response to the T-anchor 108 being at least partially covered by the cannula 410. To dissociate the sling assembly 100 from the delivery device 402, the operator can, by way of the actuator 408, move the cannula 410 in a proximal direction within the handle lumen 414 and the shaft lumen 416 to expose the covered portion of the T-anchor 108. The completely exposed T-anchor 108 can then easily disengage from the notch 406.

As in the above described illustrative embodiments, the delivery device 402 is suitable for delivering a sling assembly, such as the sling assembly 100, to an anatomical site in a patient's body by various approaches. In some approaches, the sling assembly end is associated with the delivery device 402 before inserting the delivery device 402 into the patient's body through, for example, a vaginal incision, as described above. In other approaches, the sling assembly end may be associated with the delivery device 402 after it has been inserted into the patient's body. Such approaches include, without limitation, suprapubic (abdominal), outside-in transobtural, and top-down prepubic approaches, which include inserting the delivery device 402 into the patient's body through an abdominal, ischiopubic, or other non-vaginal incision before associating it with the sling assembly end.

Referring back to FIG. 4, the shaft 404 also includes a distal tip 418. As depicted, the distal tip 418 is blunt and closed. In alternative configurations, a distal tip or distal end of a shaft may be shaped to facilitate insertion of the shaft into the tissue of a patient, for example, rounded, beveled, pointed, or any other suitable shape. Also referring to FIG. 4, the shaft lumen 416 extends distally from a distal end of the notch 406, but does not extend through the distal tip 418. In alternative configurations, the shaft 404 has a solid distal portion that extends distally from a distal end of the notch 406.

As described above with respect to FIG. 1C, in some illustrative embodiments, the sling assembly of the invention does not include anchors, such as the anchors 108 and 110 of FIG. 1A. Instead, the sling assembly may include no anchors, or alternatively, the end caps 104 and 106 may include radial projections sized and shaped for allowing the end cap to pass into tissue, but resisting being removed. Exemplary end caps/anchors that may be used with the invention are disclosed, without limitations, in U.S. Ser. No. 11/152,898, entitled "SYSTEMS, METHODS, AND DEVICES RELATING TO IMPLANTABLE SUPPORTIVE SLINGS," filed on Jun. 14, 2005, the entire contents of which are incorporated herein by reference.

In such embodiments, a delivery device shaft, such as the shaft 500 of FIG. 5, may be employed for implanting the sling assembly of FIG. 1C. As shown, the shaft 500 includes a distal section 504 and a proximal section 502. The proximal section has a diameter 510 less than the diameter 508 to form a shoulder 506.

In operation, each end cap 104 and 106 interfits one at a time over the distal section 504 of the shaft 500. The shoulder 506 inhibits the end caps 104 and 106 from sliding proximally along the shaft section 502. According to some illustrative embodiments, to such delivery device shafts may be employed, one for each end cap 104 and 106. A delivery device of the type depicted in FIG. 5C, along with other delivery devices suitable for use with the illustrative embodiment of FIG. 1C are disclosed, without limitation, in U.S. Ser. No. 10/973,010, entitled "SYSTEMS AND METHODS FOR SLING DELIVERY AND PLACEMENT," filed on Oct. 25, 2004 and in U.S. Ser. No. 11/180,167, entitled "SNAP FIT SLING ANCHOR SYSTEM AND RELATED METHODS" filed on Jul. 13, 2005, the entire contents of which are incorporated herein by reference.

Preferably, the delivery devices and/or delivery assemblies of the invention are made of biocompatible materials, which can include, for example, polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials. Preferably, a shaft of a delivery device of the invention is formed of surgical grade stainless steel.

As described above with regard to FIG. 1 and the sling assembly 100, an important advantage of the sling assembly 100 is that its length and width may be easily adjusted during a sling implantation procedure. This feature is particularly helpful when the sling assembly includes ends having an integral anchoring or other mechanism, such as in the case of the sling assembly 100. More particularly, with any useful mechanism on the sling end, it may not be desirable to cut the end off to adjust the length of the sling. Instead, the sling may need to be cut or otherwise shortened from the middle and then, in the case of cutting, rebounded together. Another important advantage of the sling assembly 100 is that since the width may be increased subsequent to insertion into the body, in an initial elongated state, it need not be wide enough to perform its supportive functions. The reduced width initial state makes it easier for the sling to travel through tunnels created by the delivery device, reducing both tissue irritation and unwanted sling deformation. Additionally, the tubular shape of the sling does not include any elongated edges that may curl, distort or otherwise deform during implantation, thus making it inherently more stable than flat, sheet like, sling counterparts.

Referring once again to FIG. 1, in an illustrative implantation method of the invention, a medical operator may employ any suitable delivery device, including those described above, to implant any suitable first anchor, such as the anchor 108 of the sling assembly 102 at a first anatomical site in the body of the patient with the sling assembly 100 in an elongated, width reduced state. Implanting the first anchor 108 essentially fixes the location of the anchor end 112a of the filament 112. Next, the medical operator places the second anchor 110 at a desired second anatomical site in the body of the patient. By adjusting the distance between the first and second anchors, the medical operator can adjust both the length and width of the sling 102, without need for any cutting, clipping or other modification to the sling 102. More specifically, as the medical operator increases the distance between the first anatomical site and the second anatomical site, the sling end 114b of the second filament 114 pulls the dilator 104 along the first filament 112 toward the second anchor 110. Similarly, the sling end 112b of the first filament 112 pulls the dilator 106 along the second filament 114 toward the first anchor 108. As described above with respect to FIG. 1, this effectively reduces the length of the sling 102. Also, due to the woven tubular configuration of the sling 102, the width of the sling increases as the length decreases. According to an alternative methodology, the medical operator fixes the location of one of the sling ends to allow only the other of the sling ends to travel along the respective filament.

According to another advantage, subsequent to implantation, the dilator 104 and 106 may continue to move along their respective filaments to change the length of the sling 102 to accommodate, for example, body movement, muscle contractions, or other physical changes in the body of the patient. This feature also effectively adjusts the tension of the sling 102 and helps to prevent the sling 102 from becoming over tensioned as result of body changes/movements.

Another important feature of the sling 102 is that its tubular configuration provides an axially extending passage 102c through which the filaments 112 and 114 pass. As shown, the filament 112 has an anchor end 112a and a sling end 112b. The sling end 112b of the filament 112 threads into the dilator 104 through the aperture 104c in the conical portion 104b, through the hollow body of the dilator 104 and out the cylindrical end 104d of the dilator 104. The aperture 104c and the filament 112, illustratively, are sized to enable the filament 112 to slide easily through the aperture 104c. The sling end 112b of the filament 112 then threads axially through the passage 102c in the cylindrically configured sling 102, through the cylindrical end 106d of the dilator 106, and anchors to the dilator 106. In the illustrative embodiment, the sling end 112b of the filament 112 is glue bonded to an inner surface of the cylindrical end 106d of the dilator 106. However, the filament end 112b may be bonded to the dilator 106 in any suitable manner and to any suitable location on the dilator 106. By way of example, the filament end 112b may be tied, heat bonded or formed integrally with the dilator 106.

In a similar fashion to the filament 112, and as shown in FIGS. 1A and 1B, the filament 114 has an anchor end 114a and a sling end 114b. The sling end 114b of the filament 114 threads into the dilator 106 through the aperture 106c in the conical portion 106b, through the hollow body of the dilator 106 and out the cylindrical end 106d of the dilator 106. The aperture 106c and the filament 114, illustratively, are sized to enable the filament 114 to slide easily through the aperture 106c. The sling end 114b of the filament 114 then threads axially through the passage 102c in the cylindrically configured sling 102, through the cylindrical end 104d of the dilator 104, and anchors to the dilator 104. In the illustrative embodiment, the sling end 114b of the filament 114 is glue bonded to an inner surface of the cylindrical end 104d of the dilator 104. However, the filament end 114b may be bonded to the dilator 104 in any suitable manner and to any suitable location on the dilator 104. By way of example, the filament end 114b may be tied, heat bonded or formed integrally with the dilator 104.

The anchor end 114a of the filament 114 attaches to the anchor 110. As in the case of the anchor 108, the anchor 110 may be of any suitable shape. In the illustrative embodiment of FIGS. 1A and 1B, the anchor 110 is cylindrical and hollow in nature, about 2 cm long and has a through aperture 110a in a side wall. The filament end 114a interfits through the aperture 110a and is bonded within the anchor 110. The filament end 114a may be bonded with the anchor 110 in any suitable manner, including without limitation, glue bonded, tied, knotted or crimped. The filament 114 is preferably formed from a flexible polymer or metal. In some illustrative embodiments, it may be formed from any suitable suturing material.

In operation, pulling on the filament 112, while holding the anchor 110 (and thus, the filament 114) stationary, pulls the dilator 106 along the filament 114 in the direction indicated by the arrow 120, causing the length 118 of the sling 102 to decrease, for example, from that shown in FIG. 1A to that shown in FIG. 1B. It also causes the diameter 116 to increase, for example, from that shown in FIG. 1A to that shown in FIG. 1B.

The inventions described herein, for example, with regard to delivery devices and anchors may be employed with any suitable sling or sling assembly, and any suitable sling delivery approach. Similarly, the inventions described herein relating to sling assemblies may be employed with any suitable delivery devices or approaches, any suitable sling assembly-to-delivery device association mechanism, and suitable anchoring mechanism or none at all.

Without limitation, examples of slings, sling assemblies, sling delivery devices and approaches, sling assembly-to-delivery device association mechanisms, and sling anchoring mechanisms including features with which the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," the entire contents of all of which are incorporated herein by reference.

What is claimed is:
1. A delivery device comprising,
a handle, and
a shaft extending distally from a distal end of the handle and including,
 a shaft lumen axially extending near a distal end of the shaft, the shaft lumen being sized and shaped for slidably receiving an anchor of a sling assembly,
 a slot extending axially along at least a portion of the shaft lumen, the slot being sized and shaped for slidably receiving a filament attached to an anchor received in the shaft lumen, and
 a notch having a width greater than a width of the slot, located along a portion of the shaft lumen, and extending axially front an end of the slot.

2. The delivery device of claim 1, wherein the shaft lumen extends axially into the shaft from an opening in the distal end of the shaft, the opening being sized and shaped for receiving an anchor of a sling assembly into the shaft lumen.

3. The delivery device of claim 2, wherein the slot extends axially in a proximal direction from the opening in the distal end of the shaft.

4. The delivery device of claim 2, wherein the slot extends proximally for an entire length of the shaft lumen.

5. The delivery device of claim 2, wherein the slot extends proximally for a portion of a length of the shaft lumen.

6. The delivery device of claim 3, wherein handle includes a handle lumen extending axially through the handle and the shaft lumen extends distally to a distal end of the shaft and axially aligns with the handle lumen, and the delivery device includes a pusher assembly, the pusher assembly including pusher and a user actuator for sliding the pusher axially within the shaft and handle lumens.

7. The delivery device of claim 1, wherein the notch extends proximally from a proximal end of the slot.

8. The delivery device of claim 1, wherein the shaft lumen extends distally to an opening in a distal end of the shaft, the opening being sized and shaped for receiving an anchor of a sling assembly into the shaft lumen.

9. The delivery device of claim 8, comprising a pusher sized and shaped for insertion into the opening in the distal end of the shaft and for extending at least to a distal end of the notch.

10. The delivery device of claim 1, wherein the notch extends distally from a distal end of the slot.

11. The delivery device of claim 1, wherein the notch is sized and shaped for receiving an anchor of a sling assembly into the shaft lumen.

12. The delivery device of claim 1, wherein a portion of the shaft lumen extends distally from a distal end of the notch.

13. The delivery device of claim 1, wherein a portion of the shaft lumen extends proximally from a proximal end of the notch.

14. The delivery device of claim 1, wherein the handle includes a handle lumen extending axially through the handle and the shaft lumen extends distally to a distal end of the shaft and axially aligns with the handle lumen, and the delivery device includes a pusher assembly, the pusher assembly including pusher and a user actuator for sliding the pusher axially within the shaft and handle lumens, at least to a proximal end of the notch.

15. The delivery device of claim 1, wherein the user actuator axially slides the pusher within the shaft and handle lumens at least to a distal end of the notch.

16. A delivery device comprising,
a handle, and
a shaft extending distally from a distal end of the handle and including,
 a shaft lumen axially extending near a distal end of the shaft, the shaft lumen being sized and shaped for slidably interfitting with an anchor of a sling assembly, and
 a notch extending axially along at least a portion of the shaft lumen, the notch being sized and shaped for receiving an anchor of a sling assembly into the shaft lumen, wherein the notch (a) is located along a portion of the shaft lumen, (b) extends axially from an end of the slot, and (c) has a width greater than a width of the slot.

17. The delivery device of claim 16, wherein the handle includes a handle lumen extending axially through the handle and the shaft lumen extends distally to a distal end of the shaft and axially aligns with the handle lumen, and the delivery device includes a cannula assembly, the cannula assembly including cannula and a user actuator for sliding the cannula axially within the shaft and handle lumens and at least partially into the notch.

* * * * *